United States Patent
Hartnick et al.

(10) Patent No.: US 8,007,435 B2
(45) Date of Patent: Aug. 30, 2011

(54) TISSUE RETRACTION DEVICE

(75) Inventors: Christopher J. Hartnick, Newton, MA (US); Michael Cunningham, Lexington, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 653 days.

(21) Appl. No.: 11/972,389

(22) Filed: Jan. 10, 2008

(65) Prior Publication Data

US 2009/0182203 A1 Jul. 16, 2009

(51) Int. Cl.
*A61B 1/32* (2006.01)

(52) U.S. Cl. ... 600/219; 600/214; 600/226; 128/200.26; 128/207.29

(58) Field of Classification Search .......... 600/184–246; 128/200.26, 207.29
See application file for complete search history.

(56) References Cited

U.S. PATENT DOCUMENTS

| | | | |
|---|---|---|---|
| 569,839 A | 10/1896 | Roeloffs | |
| 815,907 A | 3/1906 | Davis | |
| 2,002,021 A | 5/1935 | Rouse | |
| 3,750,652 A | 8/1973 | Sherwin | |
| 5,176,129 A | 1/1993 | Smith | |
| 5,776,054 A | 7/1998 | Bobra | |
| 5,899,901 A | 5/1999 | Middleton | |
| 5,988,168 A * | 11/1999 | Bair | 128/207.29 |
| 6,017,342 A | 1/2000 | Rinner | |
| 6,283,913 B1 * | 9/2001 | Seibel | 600/236 |
| 7,097,647 B2 | 8/2006 | Segler | |
| 2004/0024291 A1 | 2/2004 | Zinkel | |
| 2005/0267336 A1 | 12/2005 | Bertolero et al. | |
| 2010/0185059 A1 * | 7/2010 | Sperling et al. | 600/219 |

OTHER PUBLICATIONS

Bausch & Lomb Storz Instruments, Ragnell Retract #N4784. [online]. Bausch & Lomb Incorporated, 2007 [retrieved on Feb. 4, 2008]. Retrieved from the Internet: <URL: http://www.storz.com/productDetail.aspx?productId=2593>, 3 pp.
Leibinger Micro Implants, Instruments Cranio-Maxillo-Facial Surgery, TMJ Instruments, Self-retaining Retractors, #01-06310, Jun. 2004, Stryker France, 4 pp.
Cole, G.J., "A Self-Retaining Tracheotomy Retractor", *The Lancet*, Letters to the Editor, pp. 306-307 (Feb. 10, 1968) (2 pages).
George Tiemann & Co, "Skin Hooks & Self-Retaining Retractors," http://www.georgetiemann.com/layout.asp?include=browse&cat1=9&cat2=177&cat3=1-l036, (Feb. 7, 2001) (1 page).

* cited by examiner

*Primary Examiner* — Eduardo C Robert
*Assistant Examiner* — Christina Negrelli
(74) *Attorney, Agent, or Firm* — Fish & Richardson P.C.

(57) ABSTRACT

A self-retaining retractor is described. The retractor can be sized for small patients, such as young children or infants or some animals. The retractor has two blades that are capable of holding tissue separated during a procedure, such as a tracheotomy.

22 Claims, 8 Drawing Sheets

TISSUE RETRACTION DEVICE

TECHNICAL FIELD

This invention relates to medical devices used for tissue retraction.

BACKGROUND

Tracheotomy procedures are ideally performed by qualified medical personnel on patients who do not have and require a secure airway. To access a patient's airway, the medical practitioner typically forms an incision in the patient's neck to at least a depth at which the patient's trachea is exposed. Once the patient's trachea is exposed, any necessary procedure is performed, such as inserting ventilation tubing into the trachea. In some emergency situations, there are not sufficient trained emergency personnel available to assist with and perform a tracheotomy. Further, when the patient is a young child or an infant, the physical parameters within which the medical personnel must work are limited. Devices for simplifying and facilitating the tracheotomy procedure are therefore desirable, particularly for pediatric patients.

SUMMARY

Described herein are self-retaining retractors, for use in tracheotomy procedures, particularly in pediatric patients.

In one embodiment, a retractor device for retracting neck tissue is described. The device includes a first arm, a second arm and a connecting portion connected to the first arm and the second arm. The connecting portion is adjustable and configured to maintain an end of the first arm at a selected distance from an end of the second arm. Each arm has a blade at a distal end from the connecting portion, wherein the blade extends away from a plane defined by the first arm and the second arm, the blade is convex when viewed from a centerline of the device and the blade has a longitudinal width of at least 0.3 inches.

Embodiments of the device may include one or more of the following features. The longitudinal width of the blades can be about 0.4 inches. Each blade can have a length greater than a combined thickness of skin and muscle overlying a trachea of a child, such as a length of between about 0.4 and 0.8 inches or about 0.6 inches. The connecting portion can allow the arms to remain substantially parallel to one another as they move away from one another. The device can have a length of less than about 2 inches. The device can have a length of less than about 1.4 inches. The connecting portion can include a threaded rod connected to a hinged bar. The blade on the first arm can contact the blade on the second arm when the device is in a closed position. The blade on the first arm can be less than about two centimeters from the blade on the second arm when the device is in a maximum open position. The blade can have a radius of curvature of about 0.67 inches. The device can be formed of a biocompatible material. The device can be formed of stainless steel or resin. Ends of the blades can lack sharp or pointed surfaces. The connecting portion can include a locking feature that prevents the arms from moving away from one another. The connecting portion can include an adjustor for enabling adjustment of the distance between the first arm and the second arm, wherein the adjustor is cylindrical. A non-blade portion of the arms can have a thickness, the connecting portion includes an adjustor and the adjustor can have a thickness that is less than twice the thickness of the non-blade portion of the arms. A non-blade portion of the arms can have a thickness, the connecting portion can include an adjustor and the adjustor can have a thickness that is less than twice the thickness of the non-blade portion of the arms. The rod can extend parallel to the arms. The arms can include a bend between the blades and the connecting portion and the bend can allow the blades to contact one another when the device is in a closed state. The device can be included in a kit which also includes one or more of the following: a Bard Parker knife handle, a curved tracheotomy hook, a sharp Sen retractor, a scleral hook, a Blair retractor, a ring punch, a #5 Frasier tip suction device, a #7 Frasier tip suction devices, straight Stevens scissors, short forceps, a mosquito clamp, a small needle holder, or a jewelers bipolar forceps.

Embodiments of the devices described herein may include one or more of the following advantages. A self-retaining retracting device frees up the hands of medical personnel to assist with another aspect of the procedure. The device can ensure that the patient's tissue is held in precisely the same location for the duration of any procedure, which may not be possible with a human holding the tissue back. The device also can ensure that an assistant's hands are not in the way of the medical practitioner performing the tracheotomy. This can be particularly useful when the patient is small, such as a young child or infant. The small size of an infant's neck makes it particularly difficult for more than one set of hands to be in the same location. The self-retaining retractor can improve the practitioner's view of the trachea and may help lessen the time required to perform the procedure. When the procedure is performed in a quick and efficient manner, the likelihood of success can increase, improving the patient's chances for survival.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
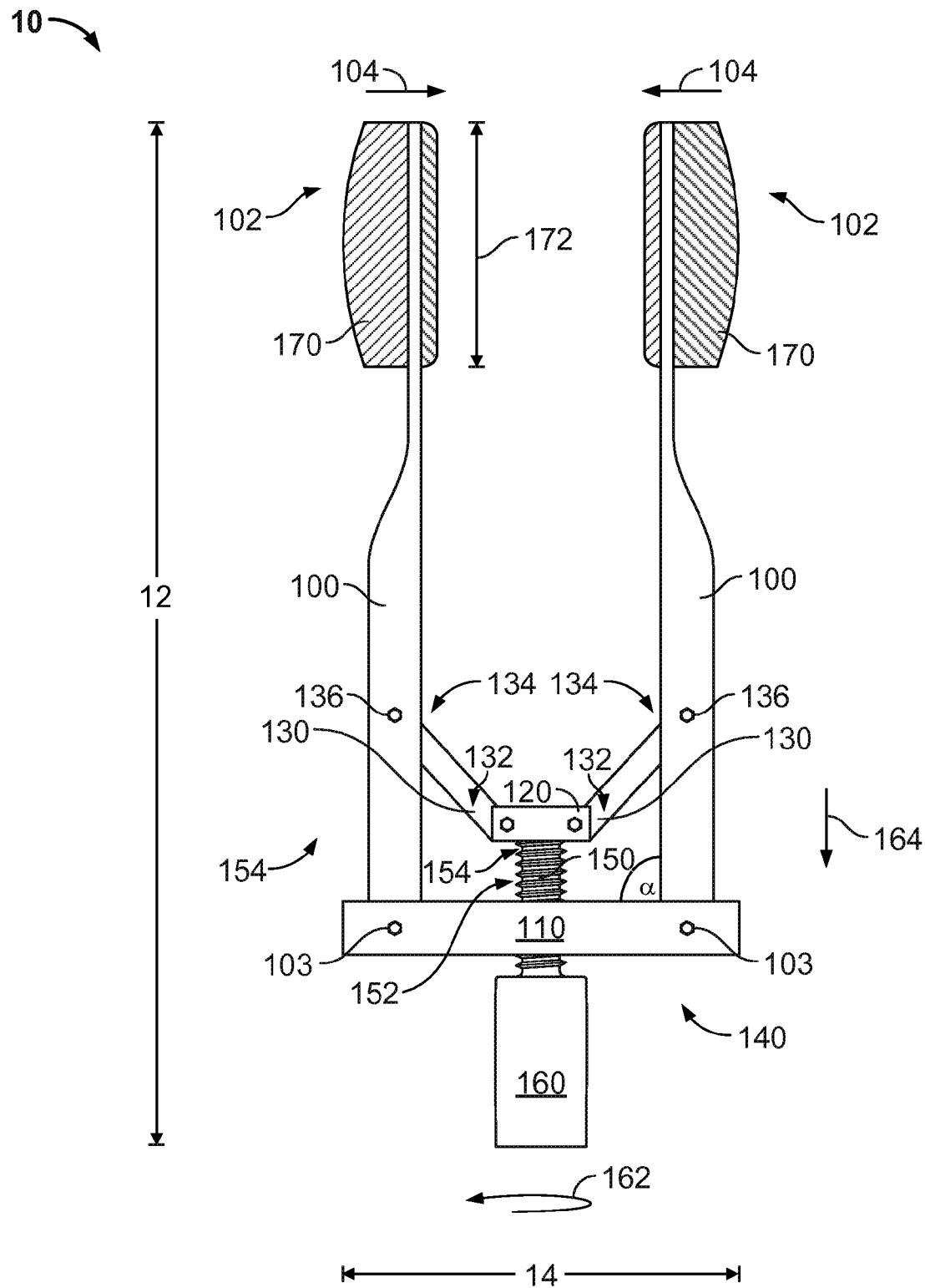
FIG. 1 is a top view of a self-retaining tracheotomy retractor.
Figure 2:
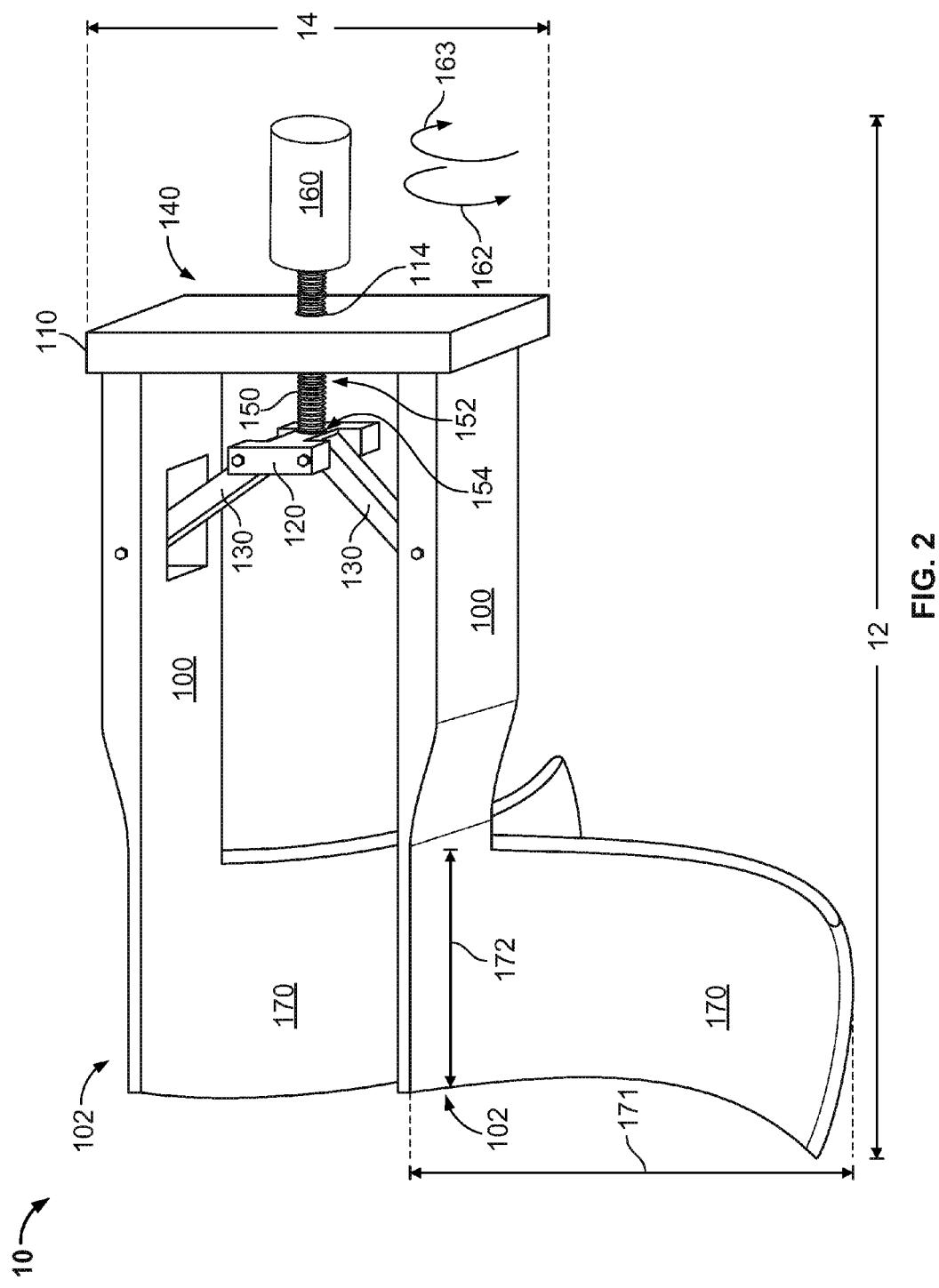
FIG. 2 is a perspective view of a self-retaining tracheotomy retractor.
Figure 3:
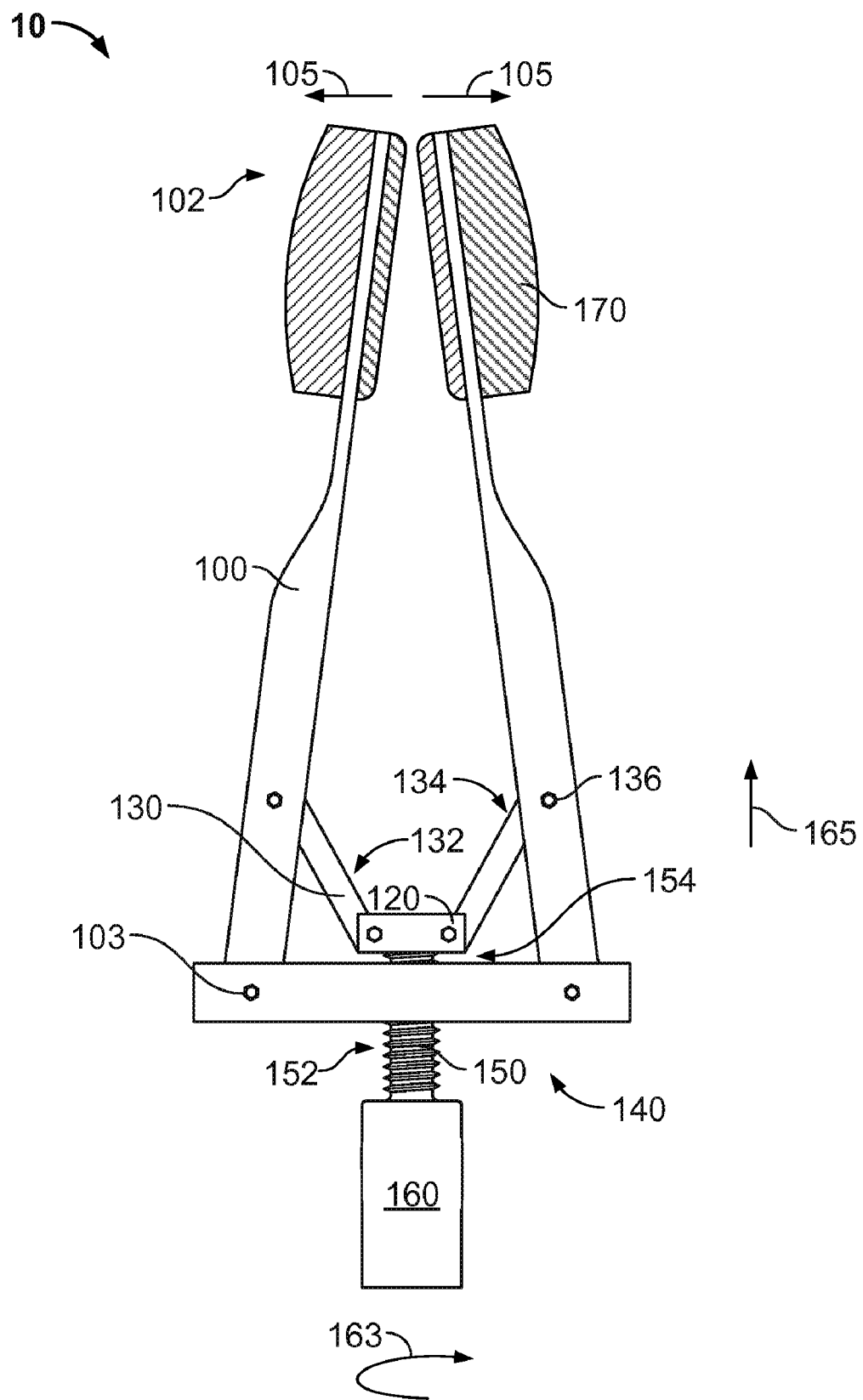
FIG. 3 is a top view of a self-retaining tracheotomy retractor in a closed position.

Referring to FIGS. 1-3, in some embodiments a self-retaining tracheotomy retractor 10 has two elongate retractor arms 100 that are pivotably mounted to the ends of and extend in a substantially perpendicular direction from a retractor base 110. The retractor arms 100 are configured to move toward and away from one another in a parallel or substantially parallel manner. In some embodiments, when the arms are closed they are at a 30° angle (α) to the retractor base 110 and when the arms are fully open then form a 120° angle (α) with the retractor base 110. Even if the arms do not move in a parallel manner, they can be parallel to one another when open to a desired width. In some embodiments, this movement is achieved with a retractor adjustment hinge 120 located between and in the same plane as the two retractor arms 100. The hinge 120 is pivotably coupled to two adjustment struts 130, which are each in turn pivotably coupled to the retractor arms 100. The adjustment struts 130, the adjustment hinge 120 and their associated pivoting mechanisms are part of an adjustment mechanism 140 which also includes a threaded adjustment shaft 150, an adjustment knob 160 and any pivot mechanisms, such as a straight bar with a boss at one or both ends, a pivot pin or any other suitable mechanism that allows two components to pivot around the pivot mechanism.

Figure 5:
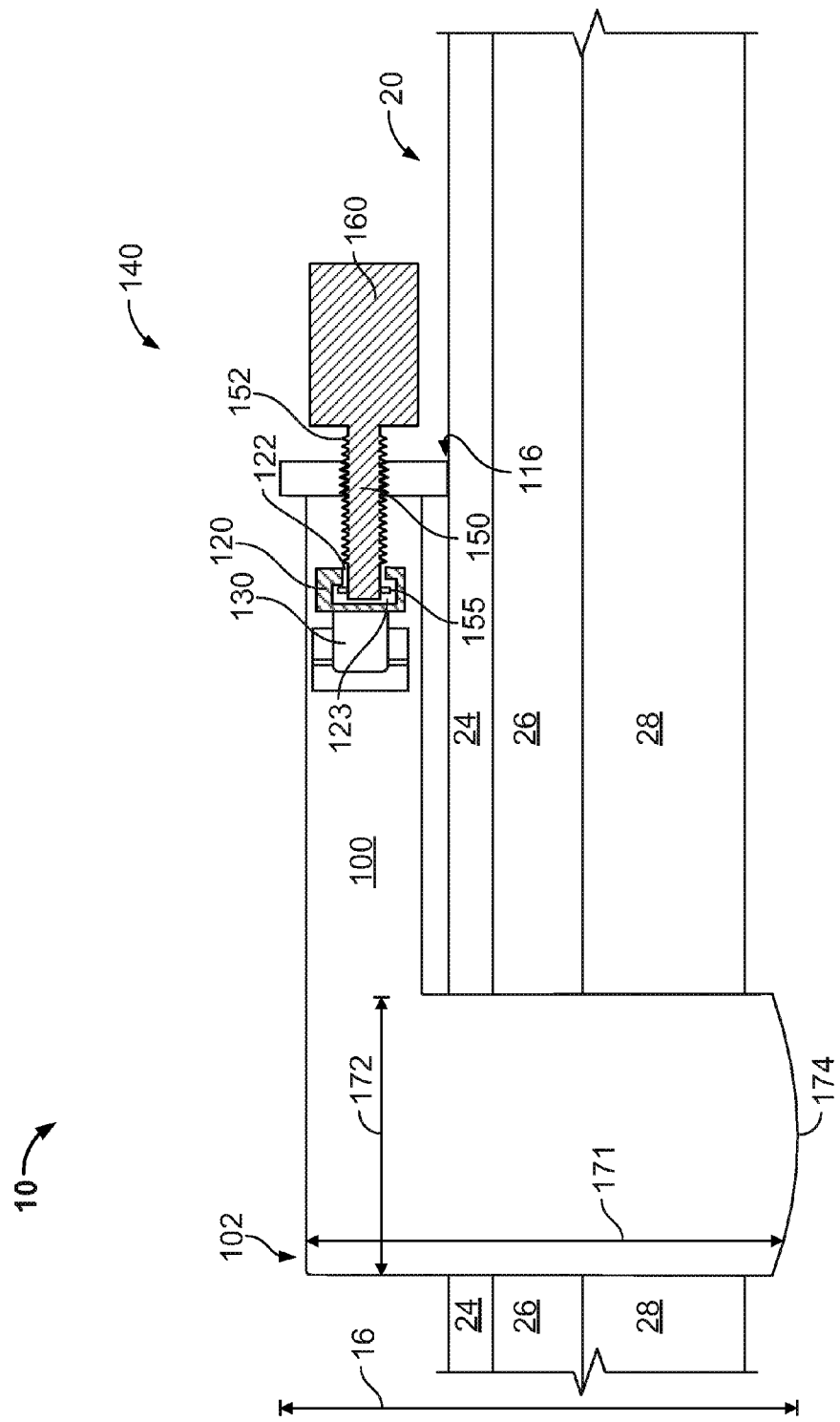
FIG. 5 is a cross-sectional view of a self-retaining tracheotomy retractor separating a patient's skin.

In some embodiments, the adjustment shaft 150 has external spiral threads 152 (e.g., extending from a distal end 154 of the adjustment shaft 150 to the base of the adjustment knob 160) that mate with a set of internal threads located in an aperture 114 through the retractor base 110. The distal end 154 of the adjustment shaft 150 can be fixed depth-wise and be rotationally coupled to the adjustment hinge 120, such that it is able to rotate within an aperture 122 (see FIG. 5) of the adjustment hinge 120, but does not translate relative to the adjustment hinge 120. That is, the adjustment shaft 150 does not move horizontally or vertically with respect to the adjustment hinge 120. The adjustment shaft 150 is fixed depth-wise within the adjustment hinge 120 so that the end of the adjustment shaft 150 can rotate within the hinge 120, but cannot be decoupled from the hinge 120. Referring to FIG. 5, the adjustment shaft 150 can have one or more circular threads 155 (as opposed to spiral threads), which fit into one or more matching circular grooves 123 in the inside diameter of the aperture 122 of the adjustment hinge 120, allowing the adjustment shaft 150 to rotate, but not translate, relative to the adjustment hinge 120.

Referring back to FIGS. 1-3, together, the components of the adjustment mechanism 140 (e.g., the adjustment shaft 150, the adjustment hinge 120, the adjustment knob 160, the adjustment struts 130, and pivot mechanisms) can be used to adjust the distance between the retractor arms 100. The threaded shaft 150 keeps the retractor 10 in a desired position until the adjustment knob 160 is rotated and a new position is selected. Retractor blades 170 located on distal ends 102 of the retractor arms 100 can extend in a direction perpendicular to the plane defined by the retractor arms 100, and can be used to retract tissue (e.g., skin, soft tissue, muscle, and the like), as described further herein. As shown in FIG. 2, in some embodiments, the top of the blade 170 is even with or substantially even with a top of the arm 100. The bottom of the blade 170 extends down from the arm and thus most of the blade extends below the arm 100.

Referring to FIGS. 1 and 3, when the adjustment knob 160 is rotated in one direction, such as a counter-clockwise direction (arrows 162), the external threads 152 of the adjustment shaft 150 interact with the internal threads of the retractor base 110 to cause the adjustment shaft 150 and the adjustment knob 160 to translate in a proximal direction (arrow 164). Because the distal end 154 of the adjustment shaft 150 is fixed depth-wise within the adjustment hinge 120 and is rotationally coupled to the adjustment hinge 120, rotating the adjustment shaft 150 does not rotate the adjustment hinge 120. As the adjustment hinge 120 translates in the proximal direction 164, internal ends 132 of the adjustment struts 130, which are pivotably coupled to the adjustment hinge 120 at pivot points 123, also move in the proximal direction 164 toward the retractor base 110. The external ends 134 of the adjustment struts 130 are pivotably coupled to the retractor arms 100 at pivot points 136 such that translation of the adjustment struts 130 pulls the retractor arms 100 toward one another. As the retractor arms 100 move toward one another, they also rotate around pivot points 103 (e.g., pivot pins) such that the distal ends 102 of the retractor arms 100 move toward each other (arrows 104). The attachment of the end of the arms to the retractor base 110 stabilizes the retractor arms and maintains their angular relationship to the base 110, preventing the ends 102 of the retractor arms 100 from swinging toward or away from one another even when the adjustment mechanism 140 is not adjusted.

In some embodiments, the pivot points 103 are at the ends of the retractor base 110 to move the retractor arms 100 in less of a scissors-like motion and more in a parallel-like motion, although it is a hybrid motion since the arms do not move perfectly parallel to one another. In some embodiments, the distal ends 102 can continue to move toward each other until the blades 170 contact each other (as shown in FIG. 3), which halts the movement of the distal end 154 of the adjustment shaft 150. In some embodiments, a stop (not shown) is located on the adjustment shaft 150 such that the stop halts the rotation of the adjustment shaft 150 just as, or prior to the point when, the blades 170 contact each other. In some embodiments, the external threads 152 end in a location that inhibits the adjustment shaft 150 from being turned beyond a predetermined point, such as the point where the blades 170 contact each other. In some embodiments, the adjustment hinge 120 contacts the retractor base 110 when the device is in a closed configuration, thereby preventing further adjustment of the blade separation.

When the adjustment knob 160 is rotated in the opposite direction, such as in a clockwise direction 163, the external threads 152 of the adjustment shaft 150 interact with the internal threads of the retractor base 110 to cause the adjustment shaft 150 and the adjustment knob 160 to translate in a distal direction with respect to the retractor base 110 (arrow 165). As the adjustment hinge 120 translates in the distal direction 165, the internal ends 132 of the adjustment struts 130 also move in the distal direction 165. The movement of the adjustment hinge 120 in the distal direction 165 causes the retractor arms 100 to rotate around the pivot points 103 (e.g., pivot pins) such that the distal ends 102 of the retractor arms 100 separate from each other (arrows 105) toward the open position depicted in FIG. 1.

Because of the external threads 152 on the adjustment shaft 150, the retractor arms remain in a desired position (e.g., in an open position) until adjusted by rotating the adjustment knob 160. That is, the retractor arms are locked in place by the adjustment mechanism. When a force (e.g., the elastic force of the tissue and muscles being held by the retractor) is applied to the blades 170 in the direction 104 that pushes the blades together (see FIG. 1), the force does not cause a rotation of the adjusting knob 160, thus there is no change in position of the retractor arms 100. This gives the retractor 10 the advantage of being self-retaining in that once the retractor is adjusted to a desired position, it will remain in that position until re-adjusted.

In some embodiments, the distal ends 102 continue to separate until the adjustment knob 160 contacts the retractor base 110, thus halting the movement of the distal end 154 of shaft 150. In some embodiments, a stop (not shown) on the shaft 150 prevents the distal ends 102 of the arms 100 from separating from one another beyond a predetermined distance. In some embodiments, the retractor arms 100 can open to a maximum of about 1 inch, such as about 0.8 inches, about 0.5 inches, or 0.4 inches apart when the retractor 10 is fully open.

In some embodiments, the retractor 10 can comprise a stainless steel material (e.g., 316L stainless steel), titanium, a cobalt alloy, such as MP35N, and/or other materials suitable for use in medical devices and devices requiring high strength. Because the retractor 10 can be intended as a disposable medical device, high strength (e.g., high tensile modulus) polymers suitable for use in medical devices (e.g., polypropylene, polyethylene, polyvinyl chloride, polyimide, polyamide, polyamide-imide, acrylic, polycarbonate, and the like) can also be used in the manufacture of the retractor 10. The retractor 10 can be manufactured in a plurality of sizes to be used on patients of varying sizes (e.g., infants, adolescents or adults).

Referring back to FIGS. 1 and 2, in some embodiments, the retractor 10 is designed to be used with infants and has an overall length 12 of between about 1.0 inch and 2.0 inches, such as about 1.4 inches. The retractor 10 can have a width 14 of between about 0.3 inches and 0.8 inches, such as about 0.5 inches and a depth 16 of between about 0.6 inches and 1.4 inches or about 1.0 inches. In other embodiments, the retractor 10 can be designed for use with larger individuals (e.g., adolescents). In these embodiments, the retractor 10 can have a an overall length 12 of between about 2.0 inches and 3.2 inches, such as about 2.6 inches. The retractor 10 can have a width 14 of between about 0.7 inches and 1.2 inches, such as about 0.9 inches and a depth 16 of between about 1.2 inches and 2.0 inches or about 1.6 inches.

In some embodiments (e.g., for use with infants), the retractor blades 170 can have a length 171 of between about 0.3 inches and 0.8 inches, such as about 0.6 inches, and a width 172 of between about 0.2 inches and 0.6 inches, such as about 0.4 inches. In other embodiments (e.g., for adolescent patients), the retractor blades 170 can each have a length 171 of between about 0.8 inches and 1.2 inches, such as about 0.9 inches, and a width 172 of between about 0.6 inches and 1.0 inch, such as about 0.8 inches. The length of the blades is not so great that damage can be done to layers of tissue that are not to be retracted.

Figure 4:
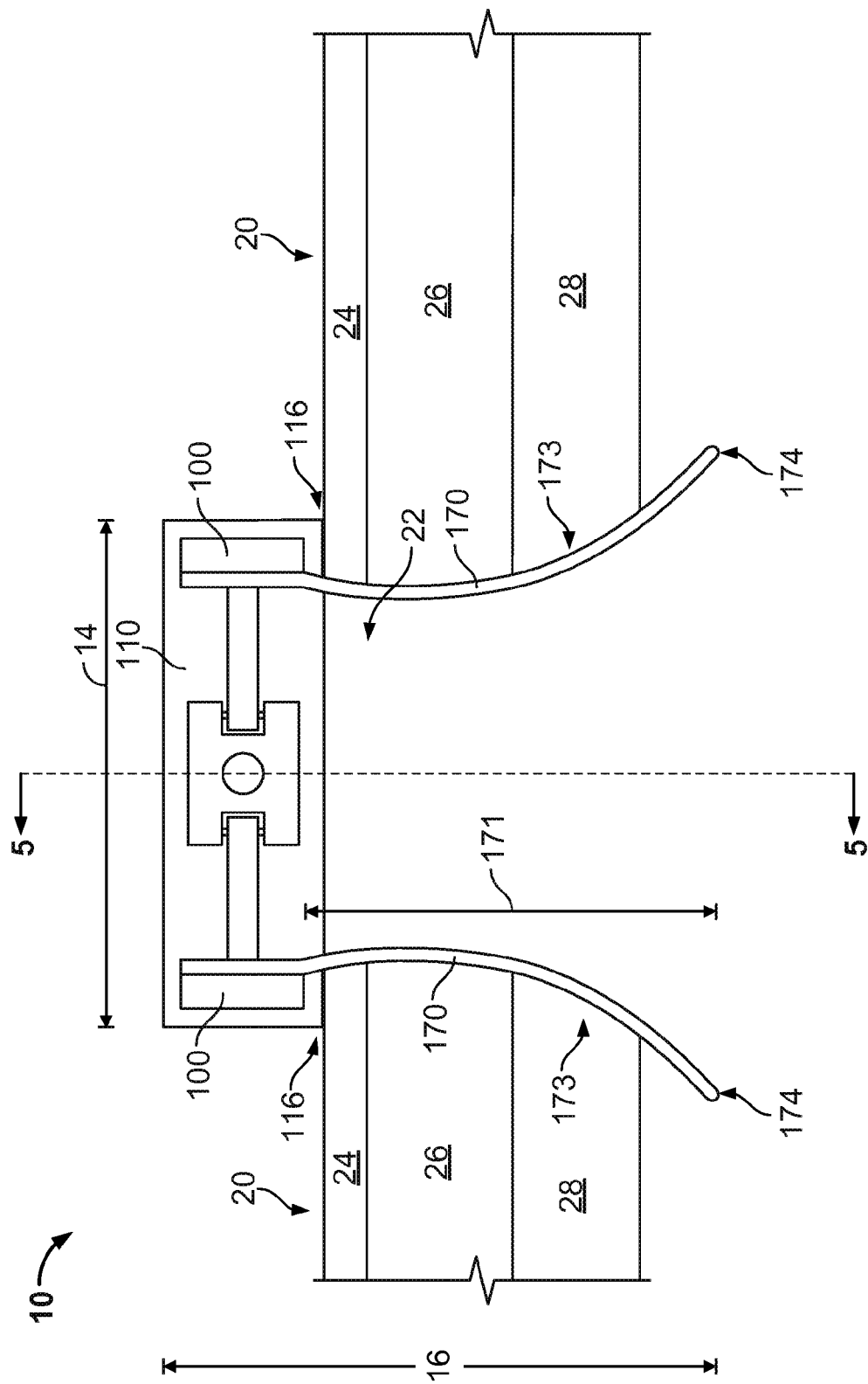
FIG. 4 is a front view of a self-retaining tracheotomy retractor separating a patient's skin.

In exemplary embodiments, the blades 170 can be shaped (e.g., curved as shown in FIG. 4) to facilitate the retraction of skin, muscle, and soft tissue (described in greater detail below). Alternative embodiments can include blades 170 that are not curved along their lengths 171, but instead are substantially straight (not shown) along their lengths 171. Other embodiments can have blades 170 that are substantially straight along a portion of their length, bend at an angle (e.g., 90 degrees), and continue in a substantially straight manner to the tips (not shown), such that from the front they look like the letter "L".

Referring to FIGS. 4-5, the retractor 10 includes retractor blades 170 attached to the distal ends 102 of the retractor arms. The retractor blades 170 are oriented and shaped to facilitate the retraction of skin 24, muscle 28, and soft tissue 26. The retractor blades 170 can include an interior radius of curvature 173 of between about 15 and 20 mm or about 17 mm or about 0.67 inches. When the blades are curved, tips 174 of the blades are further apart from one another than other portions of the blades 170. The shape and length of the retractor blades 170 allow tips 174 to pass through an incision 22 in a patient's skin 20, penetrate below tissue to be retracted (e.g., dermis 24, soft tissue 26, muscle 28), and subsequently facilitate retraction of the tissue. Once located in the incision 22, the retractor 10 can be used to retract the desired tissue creating access to tissue located below (e.g., the trachea). The blades 170 can be inserted through the incision 22 in a patient's skin 20 such that a portion of the retractor 10 (e.g., a bottom edge 116 of the retractor base 110, the bottom edge of the retractor arms 110, and the like) can be located just above and rest on the skin 20 of a patient's neck and/or upper torso.

Figure 6:
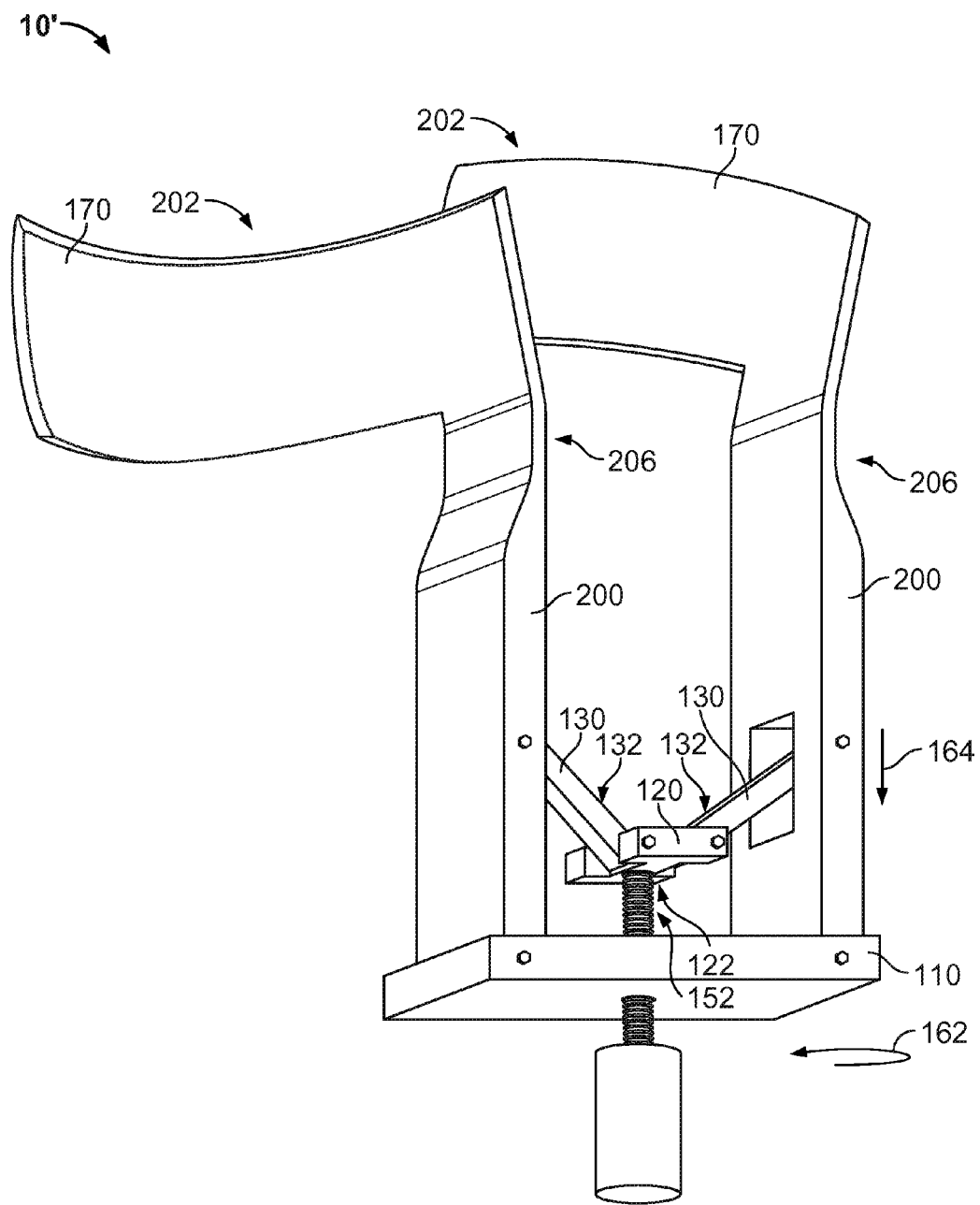
FIG. 6 is a perspective view of a self-retaining tracheotomy retractor.
Figure 7:
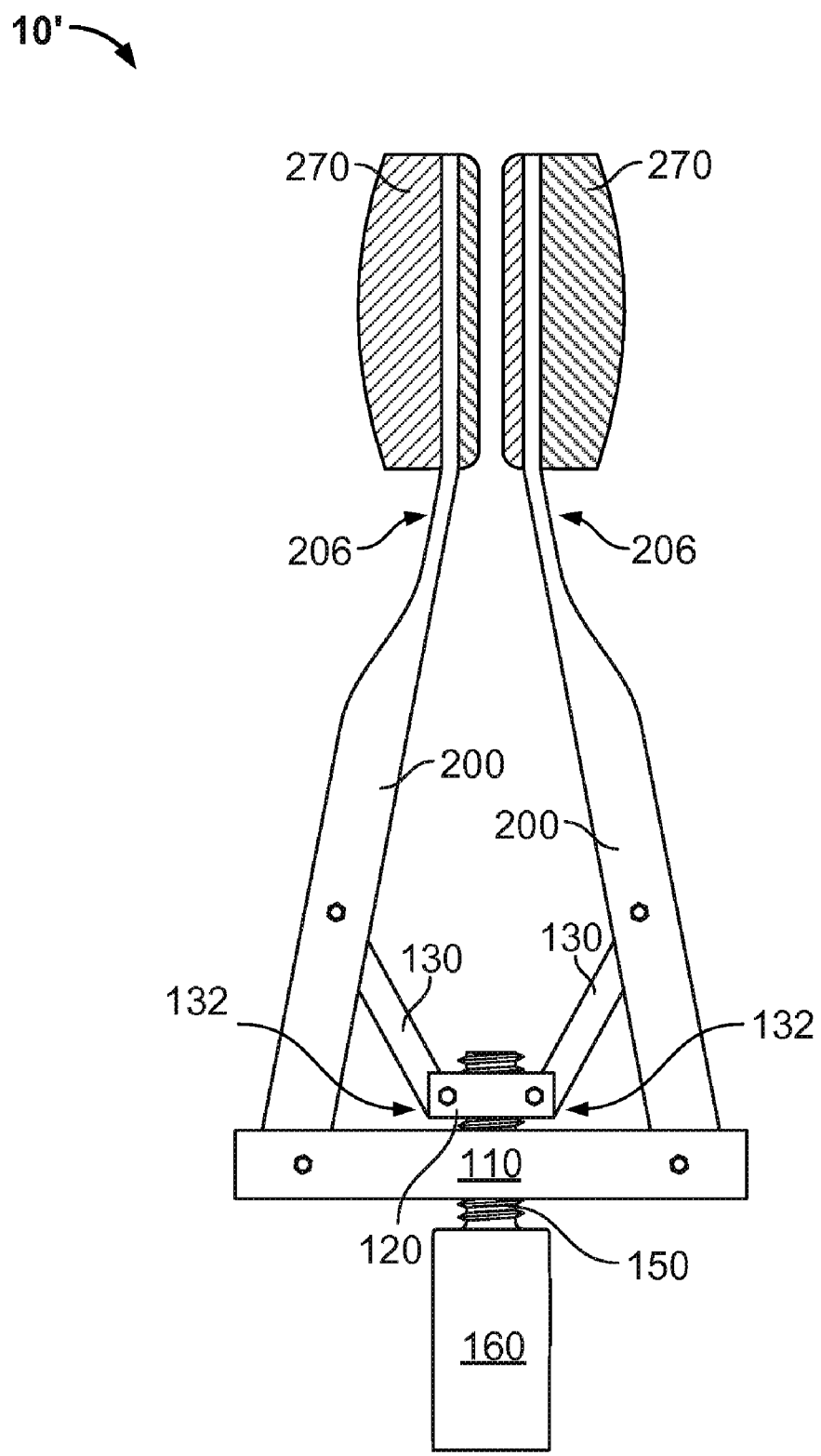
FIG. 7 is a top view of a self-retaining tracheotomy retractor.

Referring to FIGS. 6-7, in alternate embodiments, the retractor 10 can include retractor arms 200 that are outwardly curved just on the proximal side 206 of the blades 270. This curvature allows the blades 270 to be parallel to each other when the retractor 10 is fully closed (e.g., as depicted in FIG. 7). Having a back side of the blades 170 parallel when the retractor 10 is fully closed can make inserting blades 270 through an incision in the patient's skin easier. If the blades 170 extend perpendicular to the retractor base 110 when the arms 100 are extended perpendicular to the retractor base 110, as shown in FIG. 1, the blades 170 are likely to be at an angle to one another when the retractor is in the closed position. This increases the distance between the tips 174 of the blades 170 at a proximal end in comparison with the distance between the tips 174 at a distal end of the retractor. However, with a curvature in the arm 200 (FIG. 6), the distance between the tips 174 can be minimized at both the distal and proximal ends when the retractor is closed.

In some alternative embodiments of the retractor 10', the adjustment shaft 150 is rotationally coupled to the retractor base 110 in such a way that the adjustment shaft 150 can rotate, but not translate, with respect to the retractor base 110 (FIG. 7). The aperture 122 through the adjustment hinge 120 includes internal threads 124 that mate with the external threads 152 of the adjustment shaft 150. When the adjustment shaft 150 is rotated (e.g., by rotating the adjustment knob 160 with the thumb and forefinger), the adjustment shaft 150 rotates within the retractor base 110, but does not translate with respect to the retractor base 110. As the adjustment shaft 150 rotates, the external threads 152 of the adjustment shaft 150 interact with the internal threads (not shown) of the adjustment hinge 120, causing the adjustment hinge 120 to translate with respect to the adjustment shaft 150. For example, when the adjustment knob 160 is rotated, such as in a counter-clockwise direction 162, the external threads 152 of the adjustment shaft 150 interact with the internal threads of the adjustment hinge 120, translating the adjustment shaft 150 in the proximal direction 164. Because the adjustment shaft 150 is translationally fixed within and rotationally coupled to the retractor base 110 by one or more circular threads, the rotation of the adjustment shaft 150 does not translate the adjustment shaft 150 with respect to the retractor base 110, but instead pushes or pulls the adjustment hinge 120 away from or towards the retractor base 110. The movement of the adjustment hinge 120 away from or towards the retractor base 110 is due to the interaction of the spiral internal threads with the external threads 154. The adjustment hinge 120, struts 130, retractor base 110 and arms 200 all remain in the same plane when the shaft 150 is rotated because of their connections to one another.

The movement of the arms and most components of the hinge mechanism is the same as in the embodiments shown in FIG. 1, however, the end of the adjustment shaft 150 protrudes from a distal end of the adjustment hinge 120 when the retractor is closed (FIG. 7). Because the adjustment shaft 150 can rotate within the retractor base 110, but does not translate with respect to the retractor base 110, these embodiments have the advantage that rotating the adjustment shaft 150 does not cause the overall length of the retractor 10' to increase (i.e., by causing the adjustment knob 160 to extended further away from the retractor base 110).

Figure 8:
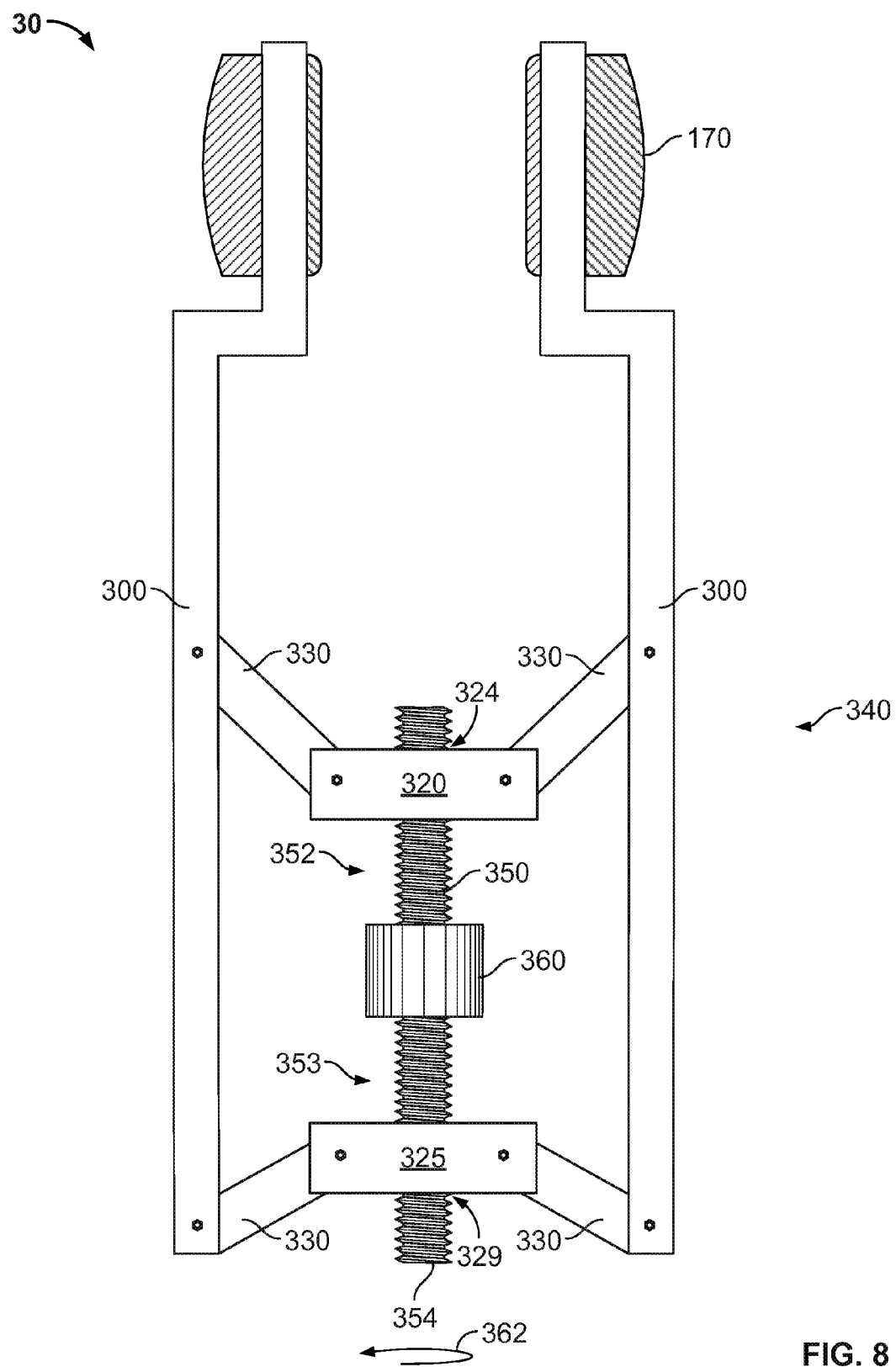
FIG. 8 is a perspective view of a self-retaining tracheotomy retractor.

Referring to FIG. 8, some alternative embodiments of the self-retaining retractor 30 include curved retractor arms 300 which are pivotably mounted to the ends of four adjustment struts 330. Located in the same plane as and between the two retractor arms 300 are a front adjustment hinge 320 and a rear adjustment hinge 325, which are pivotably coupled to the four adjustment struts 330, which are in turn pivotably coupled to the retractor arms 300. The adjustment struts 330 and the adjustment hinges 320, 325 are part of an adjustment mechanism 340 which also includes a threaded adjustment shaft 350 and an adjustment knob 360. The adjustment shaft 350 has threads 352, 353 that are oriented in opposite directions. For example, threads 352 can be left-handed and threads 353 can be right handed, or vice versa. The threads 352 mate with a set of internal threads located in an aperture 324 through the front adjustment hinge 320, while threads 353 mate with a set of internal threads located in an aperture 329 through the front adjustment hinge 325.

Together, the components of the adjustment mechanism 340 can be used to adjust the positions of the blades 170 relative to each other. Rotating the adjustment knob 360 causes the retractor arms 300 to move in a substantially parallel manner relative to each other. When the adjustment knob 360 is rotated, such as in a counter-clockwise direction 362, the adjustment hinges 320 and 325 move toward each other, causing the adjustment struts 330 to move from an orientation that is closer to perpendicular to the retractor arms 300 to an orientation that is closer to parallel to the arms 300. As the adjustment struts 330 transition to the more parallel orientation, they pull the retractor arms 300 toward each other in a substantially parallel way, decreasing the distance between the blades 170. When the rotation of the adjustment knob 360 is reversed, such as when the knob is rotated clockwise, the adjustment struts 330 transition to a more perpendicular orientation pushing the retractor arms 300 apart. In some embodiments, the adjustment knob 360 can be located on a proximal end 354 of the adjustment shaft 350 in addition to or in place of being between the front adjustment hinge 320 and the rear adjustment hinge 325. In some embodiments, a gear system (not shown) can be included to relocate the adjustment knob 360 such that it is not parallel to the adjustment shaft 350 and is instead perpendicular to the plane defined by the retractor arms 300.

To facilitate performing emergency tracheotomies, the self-retaining tracheotomy retractor can be a relatively low cost item that can come sealed, either alone as part of a kit. When packaged in a larger kit, the retractor can be part of, e.g., an advanced life support airway kit used for establishing an airway, especially in those kits made for use with pediatric patients. In an illustrative example, in an emergency setting (e.g., in an emergency room, a clinic, a physician's office, a hospital room or at the scene of an accident) a patient can suffer from a damaged airway such that a tracheotomy must be performed. Traditionally, one individual must perform the tracheotomy, while a second individual retracts the tissue covering the trachea. As a tracheotomy is a specialized procedure and not all medical personnel are trained in this procedure, it would be advantageous to need only one trained medical person instead of two or more to perform the tracheotomy. The retractor can help accomplish this by essentially freeing up one set of hands. The retractor has the additional advantage in a small patient, e.g., a young child or infant, of maintaining a desirable depth and duration of tissue refraction in a less obtrusive or obstructive fashion than when conventional devices are used.

Prior to use, the retractor can be in the position depicted in FIG. 3, where the distal ends of the retractor arms are together such that the blades contact each other. The tracheotomy procedure can be performed by someone skilled in the art, using the retractor to retract, for example, the skin, soft tissue, and muscle of the neck, exposing the trachea beneath. After performing some initial preparatory steps (e.g., positioning the patient, locally anesthetizing the neck, disinfecting the skin) an incision is made in the neck (e.g., a curvilinear skin incision along relaxed skin tension lines between the sternal notch and cricoid cartilage) followed by a vertical incision to separate the strap muscles.

The blades of the retractor are then inserted into the incision until the tips of the blades are located beneath the tissues (e.g., skin, strap muscles, and soft tissue) to be separated and such that the retractor is oriented so that the blades are closest to the head of the patient, while the adjustment knob is closest to the patient's chest. Because in some embodiments the blades are curved, the tips of the blades may need to be rotated into place. The retractor is first rotated, along the axis defined by its length, from its substantially horizontal orientation to an orientation where the tip of one of the blades is parallel to the incision and perpendicular to the plane created by the skin. The tip is inserted such that the tip penetrates below the layers to be retracted. With one of the blades in place, the retractor is then rotated back toward the horizontal position that it began in and rotated slightly such that the tissue on one side is retracted enough that the other blade can be inserted. The skin can be gently pulled back to facilitate insertion of the retractor. Once inserted, the adjustment knob is rotated, separating the distal tips and the blades from each other until the blades are separated an appropriate amount for the procedure.

Once the blades have been separated, thus retracting the desired layers of tissue the retractor can generally be allowed to rest unattended on the neck and/or upper torso of the patient while still maintaining the tissue in the retracted configuration. To remove the retractor once the procedure has been completed, the adjustment knob is rotated in the opposite direction until the blades contact each other, at which time the blades can be removed from inside the patient (e.g., using a rotating motion as described previously).

The retractor can be included in a kit with other instrumentation. The kit provides a collection of non-disposable items, disposable items or a combination of disposable and non-deposable items which are available and useful to a practitioner in the event of an airway emergency. The items may be made of metal, such as stainless steel, or a durable resin. The kit can include, in addition to a retractor described herein, one or more of the following items (and when indicated after each item, it may be useful to have multiples of each item), a Bard Parker knife handle, a tracheotomy hook (curved), sharp Sen retractors (two), scleral hooks (two), Blair retractors (two), a ring punch, #5 Frasier tip suction devices (two), #7 Frasier tip suction devices (two), straight Stevens scissors, short Debakey or Adson forceps (two), mosquito clamps (two), a small needle holder, and a jewelers bipolar forceps. The kit can include in addition to a self-retaining retractor one, two, three, four, five, six, seven, eight, nine, ten, eleven, twelve or all of the items listed above.

The design of the self-retaining feature of the retractor advantageously allows the retractor to retain skin, muscle, and soft tissue without the need for medical personnel to hold the retractor in the desired position. This frees up trained medical personnel to focus on other responsibilities (e.g., obtaining other necessary emergency drugs and equipment, etc., performing CPR, monitoring vital signs). Further, because humans are generally not able to hold perfectly still, the skin can be separated at precisely the desired distance almost indefinitely, without the risk of involving a person who can slip or tire from holding the skin in the retracted position. It also removes the second person's hands from being in the way, particularly when the patient is young and has a small neck being treated. Additionally, the retractor has the advantage of laying flush against the skin when in place, thus not interfering with the trained medical personnel performing the procedure. While the small size of some embodiments of the retractor can make the retractor ideal for use on smaller patients, such as pediatric patients, the self-retaining feature can be used in retractors of other sizes and thusly can be used for tracheotomy procedures in patients of any age. In addition, the device could be used on animals, such as dogs, cats, pigs, and other non-large animals.

A number of embodiments of the invention have been described. Nevertheless, it will be understood that various modifications may be made without departing from the spirit and scope of the invention. Accordingly, other embodiments are within the scope of the following claims.

What is claimed is:

1. A retractor device for retracting neck tissue, comprising:
   a first arm;
   a second arm; and
   a connecting portion connected to the first arm and the second arm, wherein:
      the connecting portion is adjustable and configured to maintain an end of the first arm at a selected distance from an end of the second arm wherein the connecting portion includes a threaded rod connected to a hinged bar, and
      each arm has a blade at a distal end from the connecting portion, wherein the blade extends away from a plane defined by the first arm and the second arm, the blade is convex when viewed from a centerline of the device and the blade has a longitudinal width of between about 0.3 inches and about 1.0 inches and a length of between about 0.3 inches and about 1.2 inches such that the blades are configured to retract skin, soft tissue, and muscle to expose a patient's trachea.

2. The device of claim 1, wherein the longitudinal width of the blades is about 0.4 inches.

3. The device of claim 1, wherein each blade has a length greater than a combined thickness of skin and muscle overlying a trachea of a child.

4. The device of claim 1, wherein each blade has a length of between about 0.4 and 0.8 inches.

5. The device of claim 1, wherein each blade has a length of about 0.6 inches.

6. The device of claim 1, wherein the device has a length of less than about 2 inches.

7. The device of claim 1, wherein the device has a length of less than about 1.4 inches.

8. The device of claim 1, wherein the blade on the first arm contacts the blade on the second arm when the device is in a closed position.

9. The device of claim 1, wherein the blade on the first arm is less than about two centimeters from the blade on the second arm when the device is in a maximum open position.

10. The device of claim 1, wherein the blade has a radius of curvature of about 0.67 inches.

11. The device of claim 1, wherein the device is formed of a biocompatible material.

12. The device of claim 1, wherein the device is formed of stainless steel.

13. The device of claim 1, wherein the device is formed of resin.

14. The device of claim 1, wherein ends of the blades lack sharp or pointed surfaces.

15. The device of claim 1, wherein the connecting portion includes a locking feature that prevents the arms from moving away from one another.

16. The device of claim 1, wherein the connecting portion includes an adjustor for enabling adjustment of the distance between the first arm and the second arm, wherein the adjustor is cylindrical.

17. The device of claim 1, wherein:
   the arms are pivotally connected to a first bar of the connecting portion;
   the arms are pivotally connected to a second bar of the connecting portion;
   a threaded rod extends through the first bar and the second bar; and
   rotating the threaded rod either pushes the arms apart or pulls the arms together.

18. The device of claim 17, wherein the rod extends parallel to the arms.

19. The device of claim 1, wherein the arms include a bend between the blades and the connecting portion and the bend allows the blades to contact one another when the device is in a closed state.

20. A kit, comprising:
   the device of claim 1; and
   one or more of the following: a Bard Parker knife handle, a curved tracheotomy hook, a sharp Sen retractor, a scleral hook, a Blair retractor, a ring punch, a #5 Frasier tip suction device, a #7 Frasier tip suction devices, straight Stevens scissors, short forceps, a mosquito clamp, a small needle holder, or a jewelers bipolar forceps.

21. A retractor device for retracting neck tissue, comprising:
   a first arm;
   a second arm; and
   a connecting portion connected to the first arm and the second arm, wherein:
      the connecting portion is adjustable and configured to maintain an end of the first arm at a selected distance from an end of the second arm, and
      each arm has a blade at a distal end from the connecting portion, wherein the blade extends away from a plane defined by the first arm and the second arm, the blade is convex when viewed from a centerline of the device and the blade has a longitudinal width of between about 0.3 inches and about 1.0 inches and a length of between about 0.3 inches and about 1.2 inches such that the blades are configured to retract skin, soft tissue, and muscle to expose a patient's trachea;
   wherein the connecting portion allows the arms to remain substantially parallel to one another as they move away from one another.

22. A retractor device for retracting neck tissue, comprising:
- a first arm;
- a second arm; and
- a connecting portion connected to the first arm and the second arm, wherein:
  - the connecting portion is adjustable and configured to maintain an end of the first arm at a selected distance from an end of the second arm, and
  - each arm has a blade at a distal end from the connecting portion, wherein the blade extends away from a plane defined by the first arm and the second arm, the blade is convex when viewed from a centerline of the device and the blade has a longitudinal width of between about 0.3 inches and about 1.0 inches and a length of between about 0.3 inches and about 1.2 inches such that the blades are configured to retract skin, soft tissue, and muscle to expose a patient's trachea;
- a non-blade portion of the arms has a thickness;
- the connecting portion includes an adjustor; and
- the adjustor has a thickness that is less than twice the thickness of the non-blade portion of the arms.

* * * * *

UNITED STATES PATENT AND TRADEMARK OFFICE
CERTIFICATE OF CORRECTION

| | | |
|---|---|---|
| PATENT NO. | : 8,007,435 B2 | Page 1 of 1 |
| APPLICATION NO. | : 11/972389 | |
| DATED | : August 30, 2011 | |
| INVENTOR(S) | : Christopher J. Hartnick and Michael Cunningham | |

It is certified that error appears in the above-identified patent and that said Letters Patent is hereby corrected as shown below:

Title page, Item (56) References Cited, (Other Publications), column 2, line 12, delete "2001)" and insert -- 2011) --.

Signed and Sealed this
Twenty-second Day of November, 2011

David J. Kappos
*Director of the United States Patent and Trademark Office*